US 6,554,775 B1

(12) United States Patent
Peyman et al.

(10) Patent No.: US 6,554,775 B1
(45) Date of Patent: Apr. 29, 2003

(54) ANALYSIS OF BLOOD FLOW

(76) Inventors: Gholam Peyman, 8654 Pontchartrain Blvd., Apt. 1, New Orleans, LA (US) 70124; Bahram Khoobehi, 5024 Cleveland Pl., Metairie, LA (US) 70003

( * ) Notice: Subject to any disclaimer, the term of this patent is extended or adjusted under 35 U.S.C. 154(b) by 182 days.

(21) Appl. No.: 09/717,726

(22) Filed: Nov. 21, 2000

(51) Int. Cl.⁷ .............................. A61B 5/02; A61B 5/00; G01F 1/704
(52) U.S. Cl. .................... 600/504; 600/321; 73/861.07; 424/9.6
(58) Field of Search ................................ 600/504, 312, 600/431, 321, 318; 73/861.07; 424/9.6

(56) References Cited

U.S. PATENT DOCUMENTS

| | | | |
|---|---|---|---|
| 5,106,184 A | 4/1992 | Millbocker | 351/221 |
| 5,437,274 A | 8/1995 | Khoobehi et al. | 128/633 |
| 5,687,726 A * | 11/1997 | Hoeft | 600/323 |
| 5,697,371 A * | 12/1997 | Aoyagi et al. | 600/431 |
| 5,973,779 A * | 10/1999 | Ansari et al. | 356/301 |
| 5,976,096 A | 11/1999 | Shimizu et al. | 600/504 |
| 5,976,502 A * | 11/1999 | Khoobehi et al. | 424/9.6 |
| 5,999,841 A * | 12/1999 | Aoyagi et al. | 600/431 |
| 6,351,663 B1 * | 2/2002 | Flower et al. | 250/459.1 |

OTHER PUBLICATIONS

Khoobehi et al., *Fluorescent Vesicle System: A New Technique for Measuring Blood Flow in the Retina*, Opthalmology, vol. 101, No. 10, Oct. 1994.

Peyman et al., *A Fluorescent Vesicle System for the Measurement of Blood Velocity in the Choroidal Vessels*, Opthalmic Surgery and Lasers, vol. 27, No. 6, Jun. 1996.

Shoelson et al., *Quantitative "Pseudo-Andiograms" from Fluorescent Particles in the Ocular Fundus*, Investigative Ophthalmology & Visual Science, Ab 2739–B596, vol. 39, No. 4, Mar. 15, 1998.

Khoobehi et al., *Blood Speeds and Flow Rates Mapped in the Rabbit Fundus: A Pilot Study for the Evaluation of Automated Quantification Methods*, Investigative Ophthalmology & Visual Science, Ab, 2566–B441, vol. 40, No. 4, Mar. 15, 1999.

Shoelson et al., *Automated Mapping of Blood Speeds and Flow Rates in the Ocular Fundus*, Investigative Ophthalmology & Visual Science, Ab. 2571–B446, vol. 40, No. 4, Mar. 15, 1999.

Wernet, Mark P., *Two-dimensional particle displacement tracking in particle imaging velocimetry*, APPLIED OPTICS vol. 30, No. 14, May 10, 1991, pp. 1839–1846.

* cited by examiner

Primary Examiner—William C. Doerrler
(74) Attorney, Agent, or Firm—Wood, Herron & Evans, LLP

(57) ABSTRACT

Absolute volumetric blood flow of the ocular fundus is quantified using video frames of fluorescent particles circulating in the retina and choroid. An optical apparatus is used to identify movements of particles in a passage of interest, and methods are provided for associating the individual particle movements with a blood flow rates so that absolute flow rates can be quantified.

10 Claims, 2 Drawing Sheets

ANALYSIS OF BLOOD FLOW

FIELD OF THE INVENTION

The present invention relates to in vivo analysis of blood flow.

BACKGROUND OF THE INVENTION

Recent advances in methods of studying blood flow have provided a relatively untapped resource for measuring parameters that have previously been either indeterminate or accessible only via invasive procedures. Whether these techniques use fluorescent lipsomes, microspheres, or labeled leukocytes or erythrocytes, they generally provide measures of particle position versus time; by comparing particle positions from successive video frames. One particular application of this technique is in the eye, where particle movements are used to obtain measures such as relative ocular blood flow.

While the foregoing techniques have been diagnostically useful, diagnosis of many conditions requires accurate measurement of absolute blood flow rates in areas of interest. For example, in examining ocular tissue such as the retina choroid or optic nerve head, absolute blood flow rates in capillaries can be critical in diagnosing the regulation of diseases Such as diabetes and hypertension, by providing a measurement of the dilation of veins. Absolute blood flow rate measurements are also useful in diagnosing closures of small capillaries (known as capillary dropout) and microaneurisms.

Using a scanning laser ophthalmoscope (SLO), fluorescent particles can be readily imaged in the retinal and choroidal blood vessels. However, using current techniques, the motion of particles cannot be associated with absolute blood flow rates, limiting the diagnostic usefulness of these techniques.

Accordingly, there is a need for a method of measuring absolute flow rates in passages such as retinal and choroidal blood vessels, or the entire retina and choroid, which is automated and objective.

SUMMARY OF THE INVENTION

In accordance with principles of the present invention, this need is met by new techniques for quantifying absolute blood flow. In the specific embodiment described herein, absolute volumetric blood flow is quantified using digitized video frames of fluorescent particles circulating in the retina and choroid.

In accordance with principles of the present invention, a particle counting method is used upon a subject having a known blood concentration of particles. A first step of the method is to obtain a measure of the blood concentration of particles in the subject. This measure can then be used to determine absolute blood flow, by monitoring the passage of particles in a blood vessel of interest over a period of time. A measure of absolute flow in regions of the blood vessel is then generated based upon the number of particles passing through that region over the period of time, combined with the blood concentration of particles.

In various disclosed embodiments, the measure of the blood concentration of particles may be obtained by direct measurement, i.e., by withdrawing a sample of the subject's blood and counting particles within a unit volume of the sample. As long as the particle diameters are sufficiently small compared to the blood vessels and the particles are uniformly distributed in the blood, it may be assumed that the number of distinct particles recorded in a particular vessel is proportional to the amount of blood flowing within it, and that each particle represents a given volume of blood as determined by the measured blood concentration of particles.

A measure of the number of particles passing through a vessel of interest is obtained by counting particles within the vessel during successive video frames. The counts of particles are accumulated. This count can then be converted to an amount of blood flow using the measured blood concentration of particles.

The above and other objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
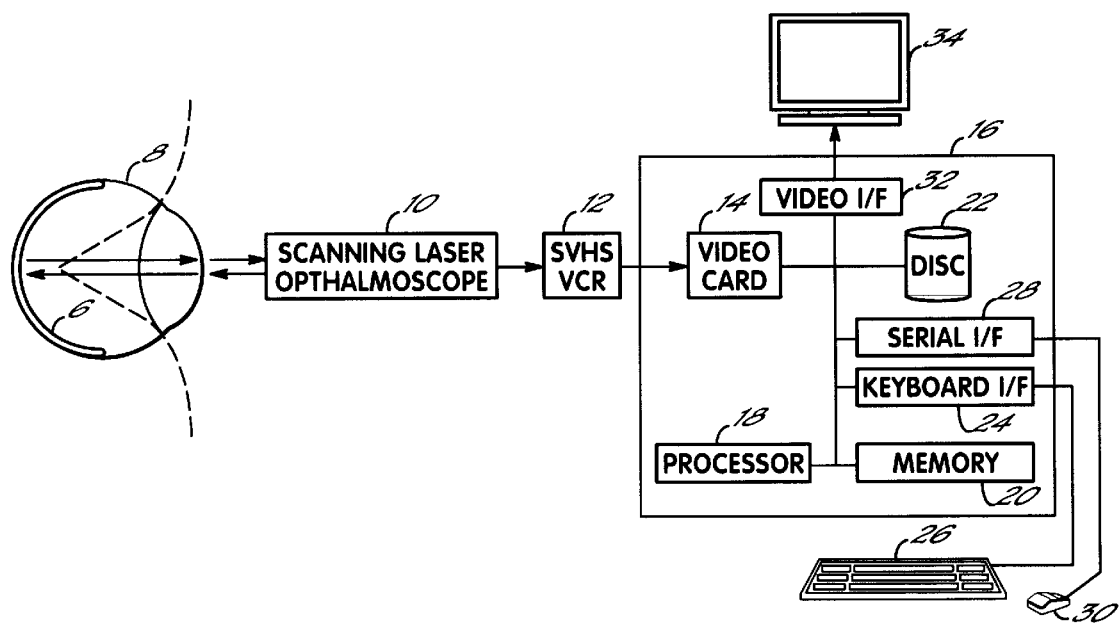
FIG. 1 is an illustration of a scanner and associated hardware for carrying out principles of the present invention in scanning the vasculature of an eye retina.

Referring to FIG. 1, a hardware configuration for carrying out principles of the present invention comprises a scanning laser ophthalmoscope SLO 101 (available from Rodenstock, Canon, N.Y. as model 101) coupled to an S-VHS videocassette recorder 12. If computer-enhanced review of images is desired, the video produced by recorder 12 can be further coupled to a digital video board 14 (available from Truevision, Inc., Santa Clara, Calif. as model Targa 2000) in an IBM-compatible dual-processor computer 16 having a Pentium P-200 processor 18 (available from Videotex Systems, Dallas). Computer 16 further comprises a suitable DRAM memory 20, hard disk drive 22, keyboard interlace 24 for interfacing with a keyboard 26, serial interface 28 for interfacing with a mouse 30, and a video interface 32 for driving a VGA or SVGA monitor 34.

The SLO images the retina 6 of a subject eye 8 using three resident lasers: a helium-neon (He—Ne) continuous wave laser of wavelength 632.8 nm and a corneal power of 0–150 $\mu$W; an argon continuous wave laser with output wavelengths of 488 and 514 nm and corneal powers of 0–500 $\mu$W and 0–250 $\mu$W, respectively; and an infrared laser module with a continuous wave 780-nm output of 0–2.0 W.

Briefly, fluorescent microsphere imaging entails positioning an anesthetized animal in front of an SLO and systemically injecting a suspension of approximately 0.03 ml of microsphere suspension per kg of body weight. The pupil is pharmacologically dilated, and the particles traveling in the ocular fundus are excited transcorneally using the resident lasers of the SLO. These lasers are focused individually or in tandem on the fundus of the eye, and spinning, multifaceted polygonal mirrors scan the laser in a raster-like fashion across the image area. The reflected light carrying the image information is "descanned" (i.e., made stationary) by a second pass through the scanning unit and sensed by the detector of the SLO. The fluorescence of the particles is then detected by the photosensor of the ophthalmoscope, while the reflected laser light is filtered. The SLO, which uses National Television Standards Committee (NTSC) recording standards, acquires images at 30 frames per second.

To facilitate simultaneous viewing of the fluorescing microspheres superimposed on the fundus vasculature, the FMI suspension can be supplemented with a low dosage of an unencapsulated dye with appropriate excitation and emission spectra. Similar results can be obtained by illuminating the fundus with a weak beam from the infrared diode laser of the In the embodiments of the present invention described below, the particles or dye carriers are red or white blood cells, that have been stained with a fluorescent dye so as to be visible within the SLO. The use of blood cells as dye carriers facilitates measurement of additional parameters such as serum blood cell percentage, as explained below. Red blood cells may be preferred for the reason that red cells are known to circulate in the body for a relatively long period of time, e.g., 20 days, allowing potentially multiple experiments based on a single injection of stained cells. As an alternative, the particles may be liposomes, which have in the past been used as dye carriers. As in fluorescent microsphere imaging (FMI), microspheres rather than liposomes may be used as dye carrier particles. Liposomes and microspheres are thus also available for use in methods of the present invention, although stained cells are presently used.

To identify an absolute blood flow rate it is necessary to associate a particle's passage through tissue of interest with a quantity of blood. To do so, it is necessary to establish the blood volume that is associated with each particle, assuming even distribution of particles in the subject's blood.

Figure 2:
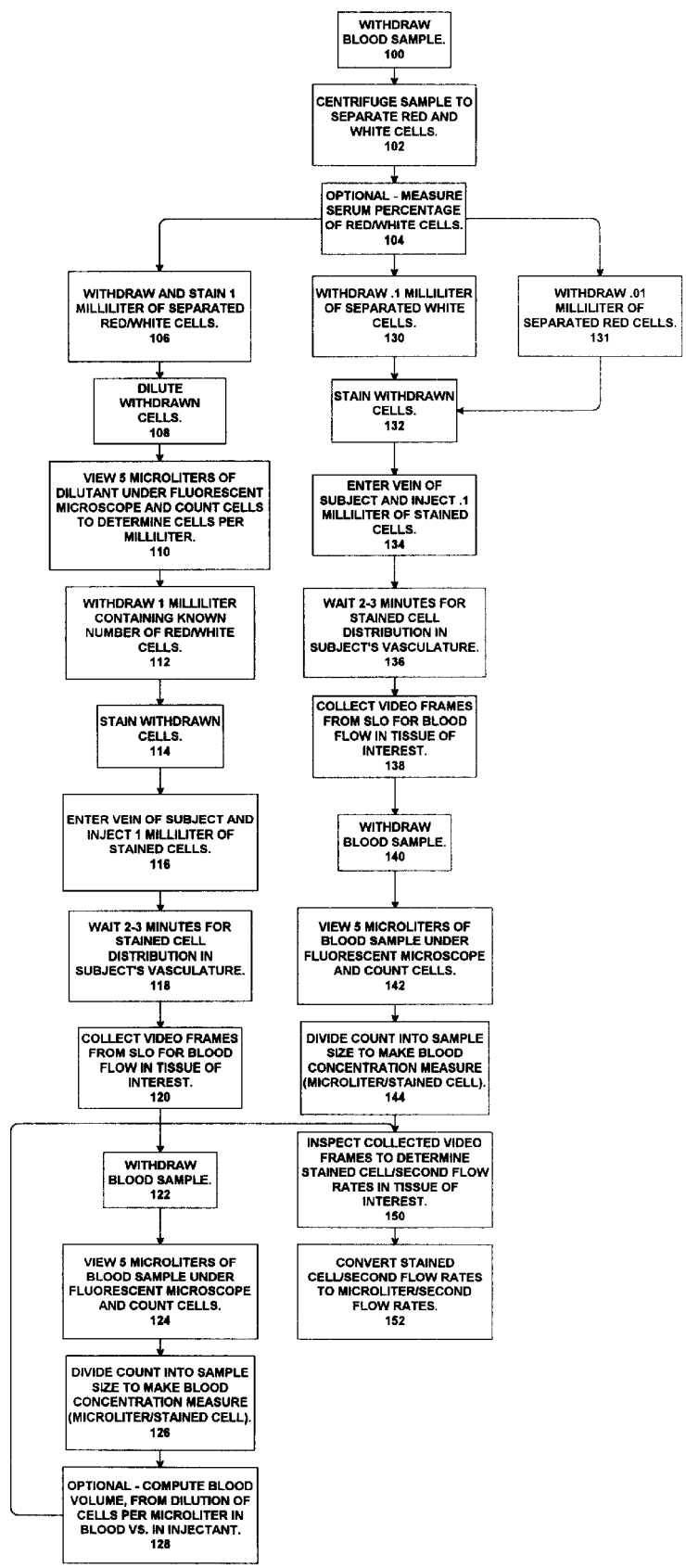
FIG. 2 is a flow chart of alternative methods for determining a blood concentration of particles and using this blood concentration in computing absolute blood flow rates using the apparatus of FIG. 1.

Referring now to FIG. 2, to solve this problem, two alternative methods are provided. Both methods use stained blood cells as particles. Thus, the first step 100 in either method is to withdraw a sample of blood from the patient. In step 102, this sample is centrifuged to separate read and white cells in the blood serum. After this step, one may optionally (step 104) measure the patient's serum percentage of blood cells.

A first method shown in FIG. 2 is directed to determining and injecting a known volume and total number of stained cells into the patient, for subsequent use in computing blood flow rates as well as patient blood volume. In this method, the first three steps 106–110 are directed to measuring the number of cells in a given volume of centrifuged blood. In step 106, a specified volume such as one milliliter of separated red or white cells is withdrawn from the centrifuged blood and stained. The withdrawn cells are then diluted in step 108, e.g. by mixture with 99 milliliters of saline. Then, in step 110, a suitable amount of the dilutant, e.g. 5 microliters, is viewed under a fluorescent microscope so that the number of stained cells in this volume of dilutant can be counted. Alternatively, cells may be counted by passing the cells through a vessel made of fiber with a 50 micron interior diameter, using a pump to push diluted blood through the vessel, so that the blood volume associated with a particle is measured dynamically in an environment analogous to where the particles are viewed in the eye. The count of cells in the dilutant can then be used to derive the count of cells in a given volume of the centrifuged blood sample. For example, if there are 250 cells in 5 microliters of the dilutant, this indicates that the entire 100 milliliters of dilutant contained 250*100/0.005=5 million stained cells, and thus the original 1 milliliter of blood contained 5 million stained cells.

After performing the above-noted calculation, steps are taken to inject a known volume and quantity of cells into the patient. Specifically, in step 112, a known volume, e.g. 1 milliliter, of cells is drawn from the centrifuged blood sample, and then stained in step 114. Then, in step 116, a vein of the subject is entered and the stained cells are then injected.

Following step 116, in step 118 a short time is allowed to pass to ensure that the injected particles are evenly distributed throughout the subject's blood system. A time period of 2–3 minutes has been found to be sufficient for distribution of the particles throughout the subject's blood.

After this time period, in step 120 images are collected from the tissue of interest and recorded in the VCR or computer as discussed above with reference to FIG. 1. The collected images can then be used later to identify flow rates through vessels of interest.

To convert the particle activity in the tissue of interest to absolute blood flow values, the blood volume associated with each particle is computed. To do this, in step 122, a sample of the subject's blood is withdrawn. Then, in step 124, a suitable sample of the patient's blood, e.g. 5 microliters, is viewed under a fluorescent microscope, or a model vessel, and the number of stained cells in this sample is counted. Then, in step 126, the count is divided into the volume of the sample, to arrive at a measure of the subject's blood concentration of stained cells, normally expressed as a number of milliliters per particle. Thus, for example, if the 5 microliter blood sample contains 5 stained cells, then it can be determined that the subject's blood concentration of particles is 1 microliter per particle.

In addition to the foregoing, an optional step 128 may also be performed to compute the patient's blood volume. Specifically, in step 128, the concentration of particles in the patient's blood sample is compared to the concentration of particles in the original injectant. In the foregoing examples, 1 milliliter of injected included 5 million particles, whereas 0.005 milliliters of blood sample contained 5 particles— which corresponds to 1000 particles in 1 milliliter of blood sample. Thus, the original 1 milliliter of stained cells was diluted 5,000 times as a consequence of injection into the patient's blood.

Thus, the patient's blood volume must be 5,000 times 1 milliliter, or 5 liters.

FIG. 2 illustrates a second, simplified method for computing the patient's blood concentration of particles. In this method, a known volume of cells is withdrawn from the centrifuged blood sample. The volume withdrawn may be, for example, 0.1 milliliter of separated white cells (step 130) or 0.01 milliliter of separated red cells (step 131). Then in step 132, the withdrawn cells are stained and then in step 134, the stained cells are injected into the patient. Following step 134, as discussed above (steps 118 and 120), a short time is allowed to pass to ensure that the injected particles are evenly distributed throughout the subject's blood system (step 136), and then images are collected from the tissue of interest and recorded in the VCR or computer as discussed above with reference to FIG. 1 (step 138). Then, as above, to convert the particle activity in the tissue of interest to absolute blood flow values, in step 140, a sample of the subject's blood is withdrawn. Then, in step 142, a suitable sample of the patient's blood, e.g. 5 microliters, is viewed under a fluorescent microscope, and the number of stained cells in this sample is counted. Then, in step 144, the count is divided into the volume of the sample, to arrive at a measure of the subject's blood concentration of stained cells, normally expressed as a number of milliliters per particle, as noted above with reference to step 128.

In this second methodology, only the volume of stained cells is known, not the number of cells. Thus, while a blood concentration measure can be made, no measure is made of the subject's blood volume.

After creating a measure of blood concentration of particles through the methods noted above, in step 150 an evaluation is made of the flow in the tissue of interest. This involves viewing sequential video frames captured by the apparatus of FIG. 1 to identify a number of particles (e.g., stained cells) passing through a vessel of interest over a given period of time. In the above-described apparatus, frames are captured at a rate of 30 frames or 60 fields per second. Thus, by viewing 30 frames, and counting the number of particles passing through a vessel of interest over these 30 frames, a measure of the number of particles per second can be created.

This measure can then be directly converted to an absolute blood flow measure, by multiplying the observed number particles per second, by the measured blood concentration in microliters per particle, to obtain a flow rate values for the vessel, expressed in microliters per second (step 152). This flow rate values may then be graphically expressed upon an image of the vasculature of the tissue, using colors to depict different flow rates, or may be otherwise depicted or presented to aid in diagnostic use.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. For example, methods of the present invention can be used to measure absolute blood flow in the entire retina, choroid, or optic nerve head, by imaging, the entire area and Counting particles passing through the entire area. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method of quantifying blood flow through a passage in a subject, comprising:

injecting particles into blood of said subject, measuring blood concentration of particles in said subject, accumulating a count of particles traveling through said passages, and combining said measured blood concentration of particles with said counts of particles traveling in said passage to derive a measure of blood flow at said locations.

2. The method of claim 1 wherein said passage is a blood vessel.

3. The method of claim 2 wherein said passage is a retinal or choroidal blood vessel or an entire retina, entire choroid or entire optic nerve head.

4. The method of claim 3 wherein said passage includes vasculature adjoining said retinal or choroidal blood vessel or an entire retina, entire choroid or entire optic nerve head.

5. The method of claim 1 wherein measuring blood concentration of particles in said subject comprises withdrawing a sample of the subject's blood and counting particles within a known volume of said sample.

6. The method of claim 1 wherein accumulating a count of particles traveling through said passage comprises comparing sequential electronic images of said passage each representing a state of said passage at different times and identifying movements of particles between said sequential electronic images.

7. The method of claim 6 wherein said sequential electronic images comprise video images.

8. The method of claim 7 wherein said video images comprise combined sequential even and odd video fields produced by a video source.

9. The method of claim 8 wherein said video source is a scanning laser ophthalmoscope.

10. The method of claim 1 wherein said particles are stained blood cells.

* * * * *

UNITED STATES PATENT AND TRADEMARK OFFICE
CERTIFICATE OF CORRECTION

PATENT NO.     : 6,554,775 B1                                             Page 1 of 1
DATED          : April 29, 2003
INVENTOR(S)    : Peyman et al.

It is certified that error appears in the above-identified patent and that said Letters Patent is hereby corrected as shown below:

<u>Title page,</u>
Item [57], ABSTRACT,
Line 6, delete "with a", insert -- with --.

<u>Column 1,</u>
Line 14, delete "lipsomes", insert -- liposomes --.
Line 16, delete "time;", insert -- time, --.

<u>Column 2,</u>
Line 47, delete "interlace 24", insert -- interface 24 --.

<u>Column 3,</u>
Line 14, delete "of the" 1$^{st}$ occurrence, insert -- of the SLO. --, end paragraph and indent "In" to begin a new paragraph.
Line 38, delete "separate read", insert -- separate red --.

<u>Column 4,</u>
Line 43, do not begin a new paragraph between "blood." and "Thus,".
Line 53, after "patient.", end paragraph and indent "Following" to begin a new paragraph.

<u>Column 5,</u>
Lines 23 and 25, delete "rate values", insert -- rate value --.
Line 38, delete "imaging,", insert -- imaging --.
Line 38, delete "Counting", insert -- counting --.

<u>Column 6,</u>
Line 10, delete "said passages,", insert -- said passage, --.

Signed and Sealed this

Seventh Day of October, 2003

JAMES E. ROGAN
*Director of the United States Patent and Trademark Office*